US007379819B2

(12) United States Patent
Betancourt et al.

(10) Patent No.: US 7,379,819 B2
(45) Date of Patent: May 27, 2008

(54) RESERVOIR SAMPLE CHAIN-OF-CUSTODY (75) Inventors: Soraya Sofia Betancourt, Cambridge, MA (US); Ahmed Hammami, Edmonton (CA); John Allan Nighswander, Katy, TX (US); Syriac George Mathews, Stafford, TX (US); Bhavani Raghuraman, Lexington, MA (US); Gale Gustavson, Brookfield, CT (US); Lennox Reid, Houston, TX (US); Tara Davies, Edmonton (CA); Oliver C. Mullins, Ridgefield, CT (US)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 11/561,167

(22) Filed: Nov. 17, 2006

(65) Prior Publication Data

US 2007/0143023 A1 Jun. 21, 2007

Related U.S. Application Data (63) Continuation-in-part of application No. 10/904,862, filed on Dec. 1, 2004, now Pat. No. 7,158,887.

(60) Provisional application No. 60/526,817, filed on Dec. 4, 2003.

(51) Int. Cl.
*G01V 1/40* (2006.01)
*E21B 49/08* (2006.01)
(52) U.S. Cl. ..................... 702/11; 73/152.28
(58) Field of Classification Search ............ 702/11, 702/12, 22, 23, 27, 30; 73/152.07, 152.09, 73/152.11, 152.23–152.24, 152.28; 175/58; 166/264
See application file for complete search history.

(56) References Cited

U.S. PATENT DOCUMENTS 5,303,775 A 4/1994 Michaels (Continued)

FOREIGN PATENT DOCUMENTS

WO 03064046 A1 8/2003

(Continued)

OTHER PUBLICATIONS

Williams, J. M., Fluid Sampling Under Adverse Conditions, May-Jun. 1998, Revue De L'Institut Francais Du Petrole, vol. 53, No. 3, pp. 355-365.*

(Continued)

*Primary Examiner*—John E. Barlow, Jr.
*Assistant Examiner*—Toan M Le
(74) *Attorney, Agent, or Firm*—Henry L. Ehrlich; Bryan P. Galloway; Wayne I. Kanak (57) ABSTRACT Methods of assuring that a representative formation and/or fluid sample of a subterranean reservoir is obtained are provided. One method of validating a reservoir fluid sample obtained from a wellbore includes the steps of acquiring a reservoir fluid sample in the wellbore; measuring a property of the fluid sample downhole with a technique to obtain a measured downhole fluid property; replicating the measuring technique used to obtain the measured downhole fluid property to obtain at a remote location from the wellbore with a technique to obtain at least one measured remote location fluid property; validating the fluid sample through comparison of the measured downhole fluid property and the at least one measured remote location fluid property.

29 Claims, 7 Drawing Sheets

U.S. PATENT DOCUMENTS

| | | |
|---|---|---|
| 5,377,755 A | 1/1995 | Michaels et al. |
| 5,394,339 A | 2/1995 | Jones |
| 5,517,427 A | 5/1996 | Joyce |
| 6,009,747 A * | 1/2000 | dos Santos ............... 73/53.01 |
| 6,343,507 B1 | 2/2002 | Felling |
| 6,352,110 B1 | 3/2002 | Langseth |
| 6,467,340 B1 * | 10/2002 | Gallagher et al. ....... 73/152.18 |
| 6,543,535 B2 | 4/2003 | Converse |
| 6,549,854 B1 | 4/2003 | Malinverno |
| 6,609,067 B2 | 8/2003 | Tare et al. |
| 6,655,457 B1 | 12/2003 | Dybdahl |
| 6,672,386 B2 * | 1/2004 | Krueger et al. .......... 166/252.5 |
| 6,714,872 B2 | 3/2004 | DiFoggio |
| 6,788,066 B2 * | 9/2004 | Wisler et al. ............... 324/376 |
| 6,799,117 B1 * | 9/2004 | Proett et al. .................. 702/12 |
| 6,925,392 B2 | 8/2005 | McNeil |
| 6,964,301 B2 | 11/2005 | Hill |
| 6,965,816 B2 | 11/2005 | Walker |
| 7,168,508 B2 * | 1/2007 | Goldberg et al. ............. 175/50 |
| 2002/0020215 A1 | 2/2002 | Nelson |
| 2002/0129936 A1 | 9/2002 | Cernosek |
| 2003/0182061 A1 | 9/2003 | Ferworn et al. |
| 2004/0098202 A1 | 5/2004 | McNeil |

FOREIGN PATENT DOCUMENTS

WO      2004106942 A2      12/2004

OTHER PUBLICATIONS

"The World Anti-Doping Code, International Standard for Testing", Version 3.0, Jun. 2003, World Anti-Doping Agency.

Williams, J.M., Fluid Sampling Under Adverse Conditions, May-Jun. 1998, Revue De L'Institut Francais Du Petrole, vol. 53, No. 3, pp. 355-365.

* cited by examiner

RESERVOIR SAMPLE CHAIN-OF-CUSTODY

RELATED APPLICATIONS

This application is a continuation-in-part of U.S. patent application Ser. No. 10/904,862 filed Dec. 1, 2004 now U.S. Pat. No. 7,158,887.

FIELD OF THE INVENTION

The present invention relates to reservoir characterization and more particularly to a reservoir fluids and reservoir formation sample chain-of-custody to facilitate data quality, management and consistency

BACKGROUND

The term flow assurance is used to describe a broad array of issues related to the reliability and operability of oil and gas production systems. The flow assurance workflow consists of two streams, a design stream and a surveillance stream. The design stream starts in the exploration and appraisal phase and ends with the commissioning of the system. The surveillance stream starts with first production and continues through the producing life of the field. The surveillance stream is a feedback loop used to monitor and optimize the production system performance.

Samples of fluid and the formation from hydrocarbon reservoirs are essential to understand the fluids to be produced. Many decisions for field development, such as production strategies and design of fluid handling facilities are based on the properties of the samples from exploratory wells. It is important to have information of the original fluids in the reservoir and the reservoir formation. Fluid samples are also acquired at later stages in the life of the reservoir to evaluate the condition of the reservoir at a certain point of time or after some production activities, however, the point of comparison is always the original reservoir properties. Thus, it is important to acquire quality, representative reservoir samples and to manage this data.

SUMMARY OF THE INVENTION

In view of the foregoing and other considerations, the present invention relates to reservoir characterization and more particularly to assuring a representative sample from a subterranean reservoir has been obtained. The reservoir sample may be a reservoir fluid and/or the reservoir formation.

In one embodiment a method of assuring acquisition of a representative sample of a reservoir formation includes the steps of acquiring a reservoir formation sample having a formation sample property; measuring the formation sample property at a point of acquisition in the wellbore with a technique to obtain a measured point of acquisition property; measuring the formation sample property at a remote location from the point of acquisition with a technique to obtain a measured remote location property; and validating the formation sample by comparing the measured point of acquisition property to the measured remote location property.

An embodiment for assuring acquisition of a representative sample of a subsurface reservoir includes the steps of acquiring a reservoir formation sample having a formation sample property; measuring the formation sample property at a point of acquisition in the wellbore with a technique to obtain a measured point of acquisition formation property; measuring the formation sample property at a remote location from the point of acquisition with a technique to obtain a measured remote location formation property; validating the formation sample by comparing the measured point of acquisition property to the measured remote location property; recording formation sample validating parameter in a database archive; acquiring a reservoir fluid sample in the wellbore; measuring a property of the fluid sample downhole with a technique to obtain a measured downhole fluid property; measuring the property of the fluid sample at a remote location from the wellbore with a technique to obtain a measured remote location fluid property; validating the fluid sample through comparison of the measured downhole fluid property and the measured remote location fluid property; and recording fluid sample validating parameter in the archives An embodiment of a method of validating a reservoir fluid sample obtained from a wellbore includes the steps of acquiring a reservoir fluid sample in the wellbore; measuring a property of the fluid sample downhole with a technique to obtain a measured downhole fluid property; replicating the measuring technique used to obtain the measured downhole fluid property to obtain at a remote location from the wellbore with a technique to obtain at least one measured remote location fluid property; validating the fluid sample through comparison of the measured downhole fluid property and the at least one measured remote location fluid property.

BRIEF DESCRIPTION OF THE DRAWINGS

The foregoing and other features and aspects of the present invention will be best understood with reference to the following detailed description of a specific embodiment of the invention, when read in conjunction with the accompanying drawings, wherein.

DETAILED DESCRIPTION

Refer now to the drawings wherein depicted elements are not necessarily shown to scale and wherein like or similar elements are designated by the same reference numeral through the several views.

Figure 1:
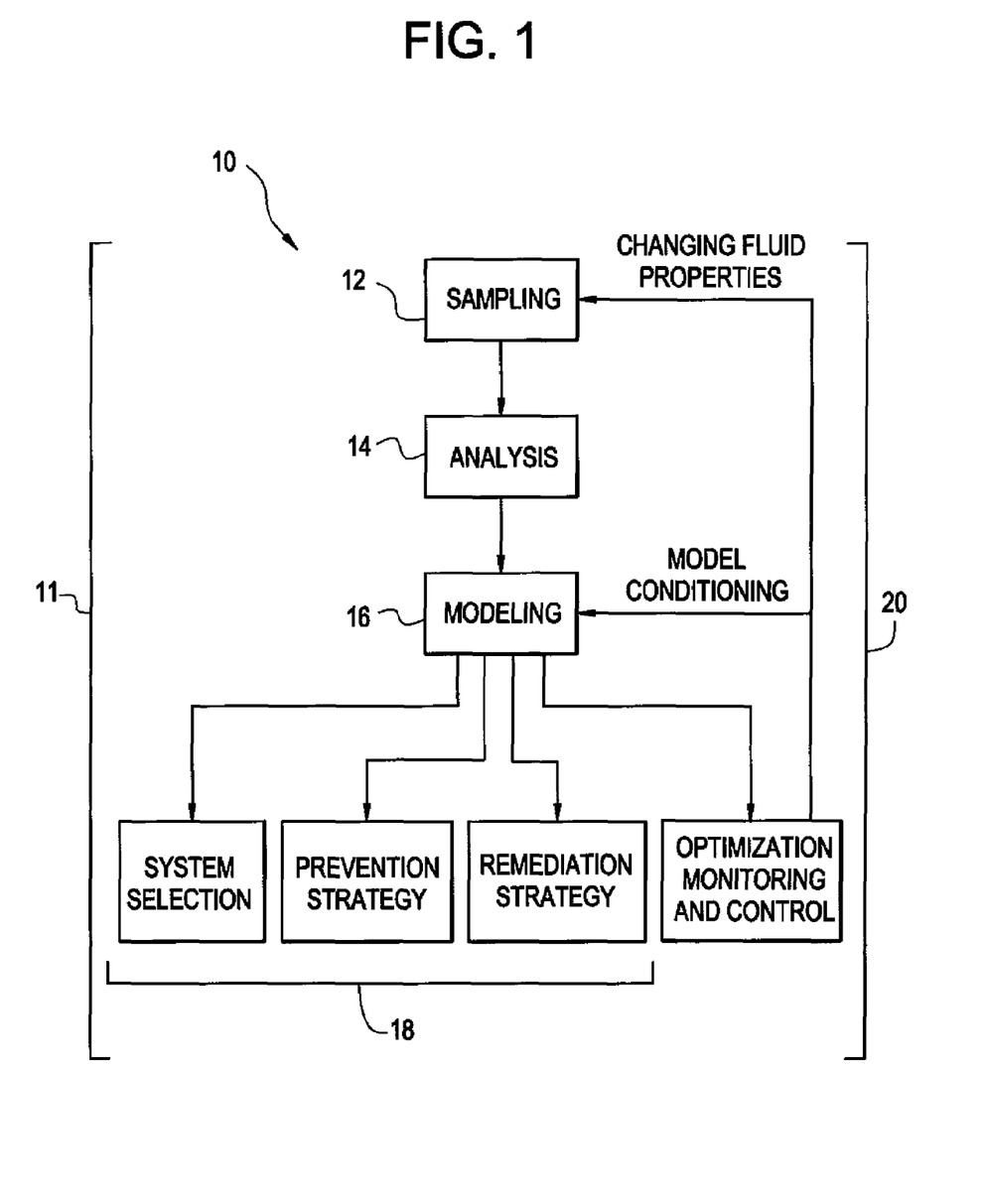
FIG. 1 is a diagram a typical flow assurance process.

Flow assurance is a critical issue that must be addressed early in the design process for production systems and is vital for offshore production systems. FIG. 1 is a diagram of a typical flow assurance process, generally designated by the numeral 10. Flow assurance process 10, as shown in FIG. 1, broadly illustrates the design process 11 including the steps of sampling 12, analysis 14, modeling 16 and design 18; and the surveillance process 20.

The process starts in the exploration and appraisal phase where in-situ fluid and formation property data are measured and selected samples are retrieved for more detailed analysis. Specific flow assurance related studies may be run on the fluid and reservoir samples in the laboratory. The scope and type of these analyses will depend on the anticipated problems. The laboratory data is then used in a series of engineering software tools to model various scenarios for the production system. From that process, each system and its appropriate flow assurance management strategy is defined.

Once the selected system is designed and installed, the flow assurance management processes should be monitored and optimized in a surveillance process. Recognizing that the initial design of these strategies was most likely conservative, there are typically good opportunities to optimize the process. However, the large cost of failure requires a careful monitoring of the system to catch potential problems before they result in a catastrophic failure. In the surveillance process, system data like temperatures, pressures and flow rates are collected from sensors at various points. Models that use fluid or formation property data obtained in the design phase are conditioned to the measured system data. These models can now be used to determine the current state of the system and to optimize the system through a series of runs.

The design and surveillance work streams should fit seamlessly together and must be consistent. The same data sets and models used for the system design should be used for monitoring and optimization. In the following, we will describe each element of the workflow process in more detail.

Figure 2:
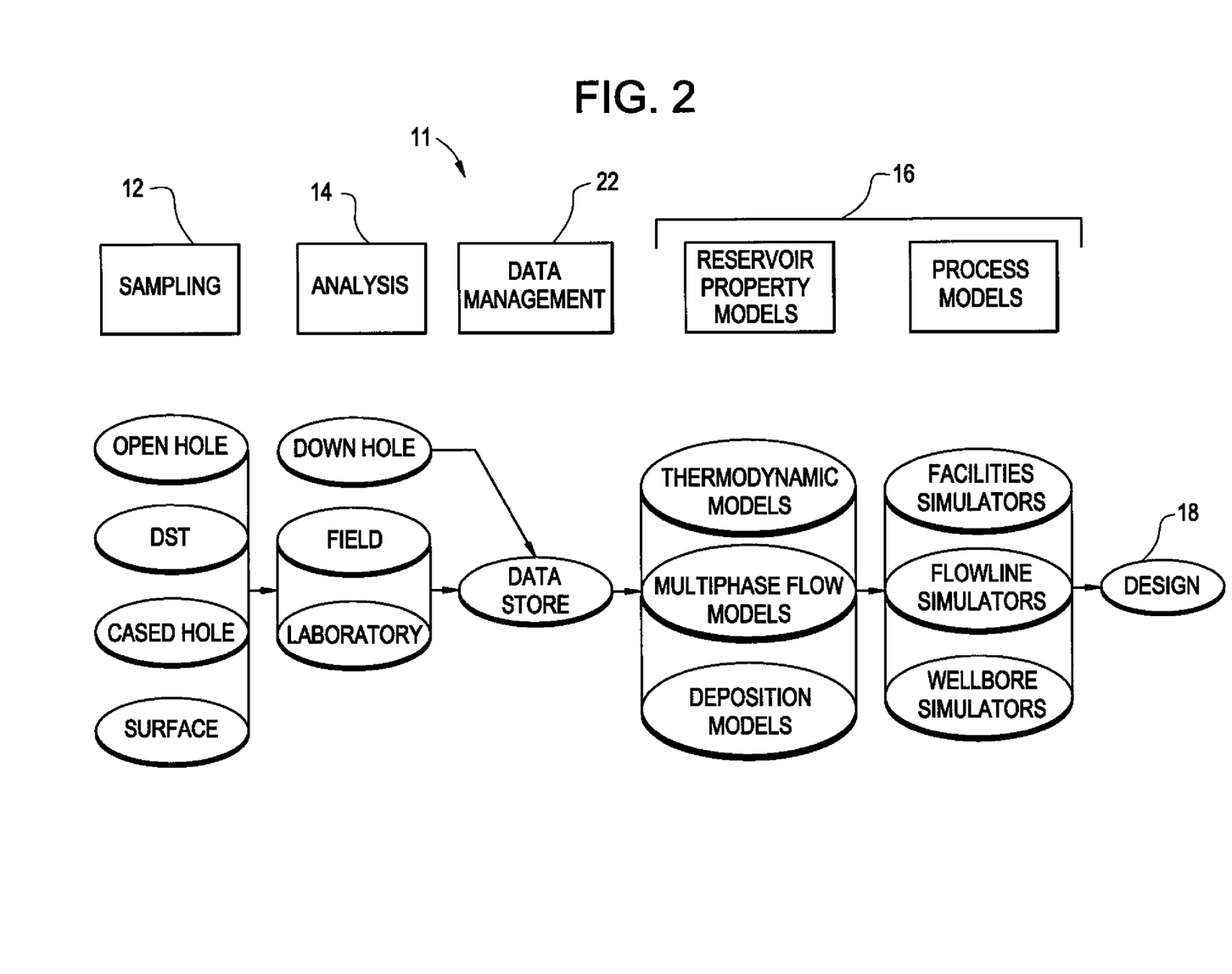
FIG. 2 is a diagram of a design process of a flow assurance process.

FIG. 2 is a diagram of a design process 11 of the present invention. Subsurface sampling 12 is the first step in design process 11.

Flow assurance measurements have led to a new awareness of the need to have representative samples. The goal of any sampling procedure is to bring a sample back to the lab that is identical in composition as when it is in the reservoir. Unfortunately, many of the solids that cause flow assurance problems come out of solution during the sampling process just as they do in production systems. Changes in pressure and temperature can cause phase changes that lead to sample alteration. Introduction of contaminates during the sample acquisition process can also alter the fluid composition. The most common source of contamination is from drilling fluids.

The reservoir sample may be acquired by obtaining sidewall cores from the reservoir formation. The subsurface in-situ testing (conducted in the coring tool) provides the opportunity to compare the downhole measurements to measurements on the core in the lab to confirm the provenance of the core and determine whether the core sample has undergone a transformation since being obtained.

The perfect sample would be collected contamination free from the reservoir at constant temperature and pressure and transported intact to the laboratory maintaining both temperature and pressure. In this way alteration associated with phase changes, transfers or contamination is eliminated. In practice, this is not possible today. A more realistic goal is to reduce the potential for phase changes through pressure and temperature compensation.

The sample data such as, but not limited to, date of sample, serial number, sample number, log file, depth of sample, sampling method and tool configuration, formation pressure, formation temperature, mud type, type of sample bottle, sample temperature and pressure at time of bottling, fluid sample composition, gas-oil ratio (GOR), level of contamination, density, viscosity, H2S concentration, saturation pressure, water pH, and spectroscopic fingerprinting of the sample (visible-near-infrared (VI-NIR), fluorescence, reflectance) may be recorded. This data may be stored in the data management system 22. Data management system 22 may be a software based, electronic system.

At the analysis stage 14, relevant flow assurance related fluid properties of the samples are measured. The fluid analysis can be done downhole, in the field and/or in the laboratory. The list of relevant fluid properties will vary depending on the type of fluid and the expected system operating conditions. Typically, a phased approach to the design of an analysis program is taken. Sample conditioning and validation is done first. This usually consists of composition and basic fluid properties. Once samples of sufficient quality are identified, flow assurance screening is done.

Examples of wax, asphaltene and hydrate screening are illustrated. For wax, the following are measured on a dead oil: the normal paraffin distribution, using high temperature gas chromatography (HTGC), wax appearance temperature, viscosity and pour point. If these parameters indicate potential wax deposition, elevated viscosity or gelling problems, a more thorough analysis program including measurements made under live oil line conditions and chemical evaluation is needed.

For asphaltenes, dead oil characterization data including SARA (Saturate Aromatic Resin Asphaltene) and paraffinic solvent (typically n-pentane or n-heptane) titration endpoint are used as screens for fluid stability. Because asphaltene screening and modeling capability is less well developed than those for wax, it is common to measure at least one live oil asphaltene precipitation pressure as well. If an asphaltene issue is identified, additional studies are defined to map out the Asphaltene phase diagram as a function of temperature and to evaluate the effectiveness of chemicals or coatings as prevention strategies.

For hydrates gas, composition from a standard PVT or validation study and water composition are used in a thermodynamic model to generate the expected hydrate formation boundary. If the compositional data are unusual or the pressure and temperature conditions are outside the range of validity of the model, direct measurement of hydrate formation conditions may be performed. If a potential problem exists a combination of models and experimental data are used to evaluate the performance of thermodynamic inhibitors and/or low dosage inhibitors (LDHI).

In the analysis stage 14, various reservoir formation properties and/or geochemistry properties may be obtained downhole. For example, core mass density data may be obtained by gamma ray attenuation performed in the sidewall coring tool. The photo-electric effect of the core sample may be obtained downhole by measuring the energy dependence of the gamma ray attenuation particularly at low gamma ray energy. Other downhole core measurements may include NMR, acoustics, optical, and electromagnetic. Additionally, fluid flow through the core sample may be measured downhole.

Some of the reservoir formation sample properties may be bulk measurements of the formation sample and some may provide a spatial dependent signal. In particular, as the core is pushed through the core barrel, it may be scanned by a stationary source such as a detector pair. Thus, a core property measurement as a function of linear position along the core may be obtained. NMR measurements conceivably can image part or all of the core sample.

The downhole core analysis (DCA) measurement of the core property provides a finger print of the core. When the core goes to surface or the lab, the same measurement in the same configuration can be measured. This allows validation of the core sample prior to measuring sundry core properties in the lab. In addition, the comparison of the DCA measurement downhole with its equivalent in the lab allows determination if the core has undergone a deleterious change since being retrieved downhole. If the DCA measurement differs in a meaningful way with the corresponding lab measurement, then the core sample may have become invalid. For example, once all confining pressure is released, the core could fracture due to contained pressure. If the DCA—lab comparison indicates a deleterious alteration, then measurements on the core would be viewed as suspect.

Cores brought to surface typically exhibit effects from released confining and released pore pressures and fluid movements. Frequently, the core dries out changing wettability, clay properties etc. The goal of DCA would be to identify such effects. Chain of Custody on cores would strive to monitor whether any of these alterations might have occurred.

The area of flow assurance measurements is still a developing field with new technologies becoming available regularly. This has both positive and negative consequences. On the positive side, the ability to measure and interpret changes in fluid and formation behavior is continually improving. This leads to a better design that both optimizes performance and reduces flow assurance risks. However, the dynamic nature of the measurement technology has led to a lack of standardization and inconsistencies between measurements and modeling.

In data management 22, all sampling and downhole sample analysis data are stored in a central database, such as a web-based system. The database may contain sampling logs, transfer and shipping information, and all downhole, field and laboratory property measurements. Database management provides several functions: management of data and a data management service to clients; a web based data delivery system for client data and reports; ability to track sample quality by easily comparing multiple measurements made during the sampling, handling and analysis process and by tracking the sample history (this is a chain-of-custody service); and it can transfer data directly to the reservoir property models.

The modeling step 16 may include reservoir property models and process models. The reservoir property models include, but are not limited to, thermodynamic, deposition and multiphase flow models. The property models are the connection between the analytical sample data and the engineering application. All of these models use measured data available in the reservoir property database. For the thermodynamic model experimental data for fluid properties and phase behavior are loaded into the thermodynamic package. Equations of state parameters are tuned to match the measured values. The model parameters may then be stored in the database along with the sample properties used to generate them. Deposition and multiphase flow models use sample property data in the database directly. Again it is important to remember that models should have been developed using the same type of experimental data stored in the database. That is, sample type and quality and analytical technique and procedure of the data must be consistent with that used to develop the models. With the data management process and integrated approach of the present invention this is assured.

The reservoir property models are embedded in industry standard engineering packages. Packages used to design production systems include, but are not limited to: reservoir simulators; well bore simulators; flow line simulators and process or facilities simulators. Much effort has been directed towards incorporation of the same set of fluid property models across the different types of simulators. In this way, reservoir properties will be modeled consistently in the various parts of the production system.

In design step 18, the models are utilized in the pre-feed and feed stages of engineering design to select the type of production system and develop operational procedures. At this stage, prevention and remediation strategies for common flow assurance problems are developed. Part of the study may include procedures for start up and shut down. In the detailed design phase the models may be revisited and adjusted to reflect the final system design.

Figure 3:
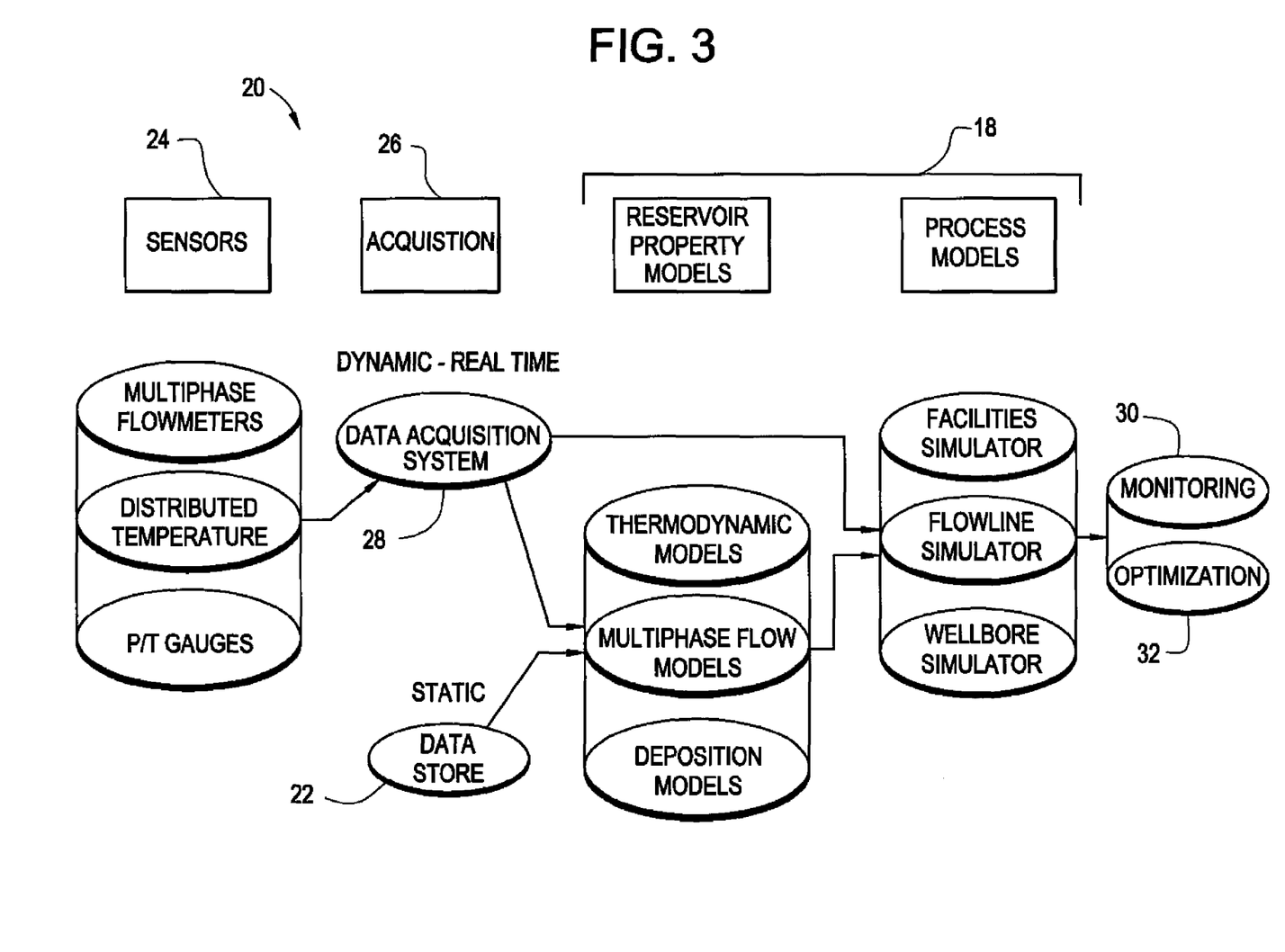
FIG. 3 is a diagram of a surveillance process of a flow assurance process.

FIG. 3 is a diagram of a surveillance process 20 of a flow assurance process of the present invention. Surveillance 20 starts with first production and continues throughout the producing life of the field. It is initially based on the data and models used in design process 11. These models and data may change over time to reflect changes in the system.

Data is acquired 26 from two sources. Sensors 24 within the system measure data related to system performance (dynamic-real time data). These measurements may be real time or periodic. A variety of sensors 24 are currently available that are important to flow assurance monitoring. They include discrete pressure points, discrete and distributed temperature, phase flow rates and chemical injection rates. These measurements are stored in a database 28.

The second source of data is reservoir property and flow assurance data (static data) collected prior to the design stage 11 and maintained in a static data store 22. As in the design stream 11, reservoir property data in the static store 22 must be complete and consistent with the models used for surveillance. That implies that well before the system is ever installed one must consider how flow assurance strategies will be monitored 30 and optimized 32. It is essential to take all the required data as wells are drilled and representative samples can be obtained easily. Once the system is on production it is much more difficult and costly to collect high quality flow assurance samples within the subsea domain.

If fluid composition changes over time, the static fluid property data still may be periodically updated. Composition may change during depletion. For example, as a gas condensate falls below the saturation pressure both the condensate yield and the wax appearance temperature may fall. In a compositionally graded accumulation, composition may change as fluids from regions away from the initial sample point are produced. New fields or zones being brought into an existing production system can also change the fluid properties within the system. The fluid property data set must be updated to reflect these changes.

The same engineering models 18 used to design the system are used to interpret the performance of the system. The models must be conditioned to the measured data. The less data available for the system the less constrained the conditioning or tuning will be, thus increasing the uncertainty associated with the non-unique nature of conditioned model.

Consider the following simple example. Inlet and outlet temperature of a section of flowline are different than predicted by the model. Is the overall heat transfer coefficient, U value, along the length of the line uniformly different from the assumed value or is there a smaller section along the flowline where the insulation has failed and elsewhere the assumed U value is appropriate? This may have implications for wax deposition. If the heat transfer coefficient is significantly higher over a short section of flowline there will be a much lower wall temperature in this region, which would lead to an enhanced wax deposition rate. A distributed temperature measurement (temperature every few meters) along the flowline would supply more detail and be able to eliminate or confirm this possibility. Therefore, additional resolution in temperature data results in a conditioned model with less uncertainty.

Figure 4:
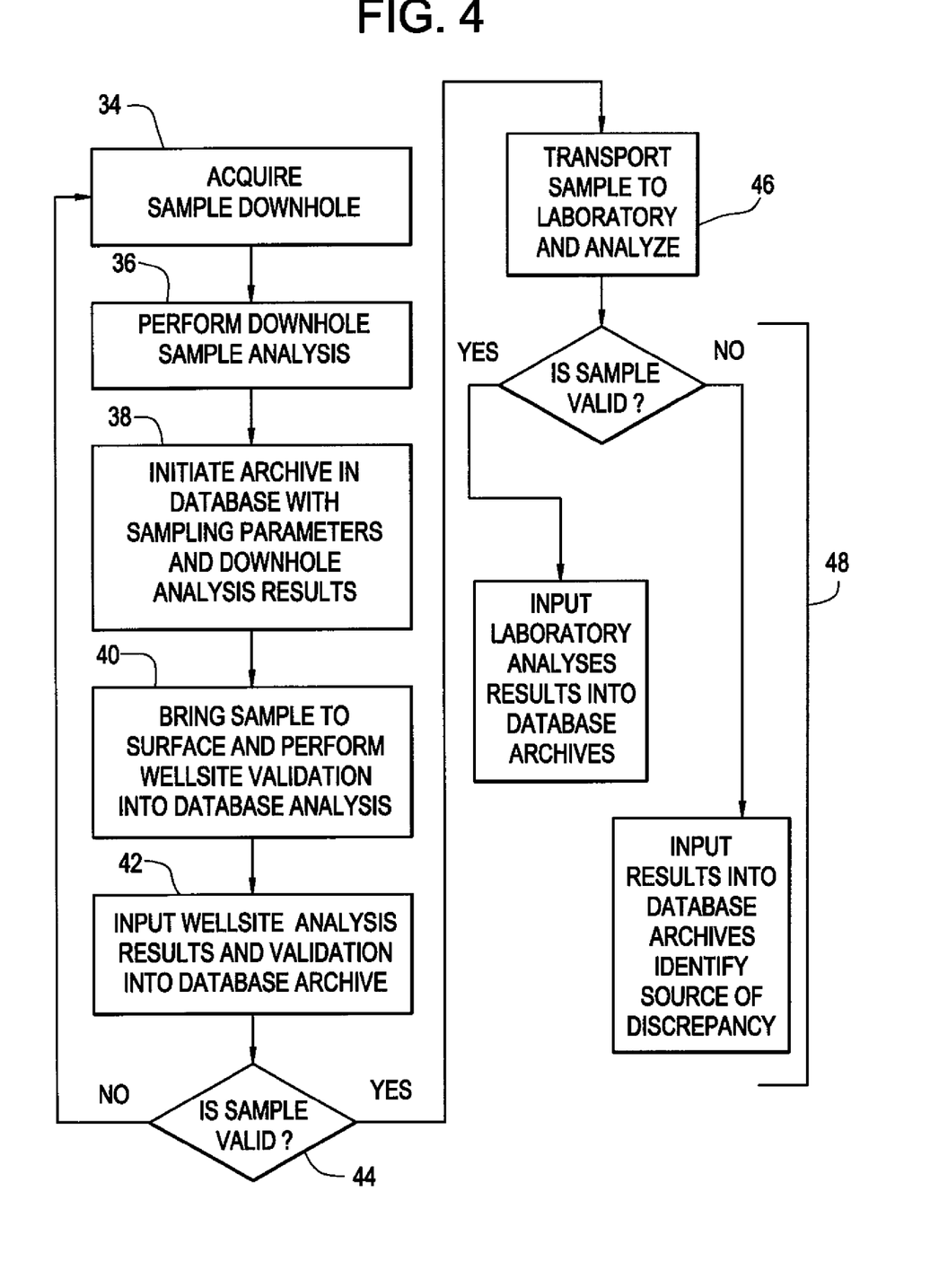
FIG. 4 is a flow chart of a reservoir sample chain-of-custody of the present invention.

FIG. 4 is a flow chart of a reservoir sample chain-of-custody of the present invention. Chain-of-custody refers to the process by which fluid samples are acquired and properties are measured to obtain valuable information for reservoir development. The process includes monitoring fluid property measurements at different stages between and during sample collection and laboratory analysis. More specifically a purpose of the invention is to link downhole, subsea, wellsite, surface facility, and laboratory analyses results into a single data management system, and to facilitate quality control and quality assurance.

A reservoir sample chain-of-custody method begins with acquiring 34 a fluid sample and or a core sample of the reservoir formation. The fluid sample may be obtained at reservoir depth (downhole), at the wellhead, or at a separator. Measurement 36 in-situ of select physical and chemical properties of the fluid sample are performed. The reservoir formation sample is obtained at reservoir depth utilizing a tool such as a sidewall coring tool. Measurement 336 in-situ of select physical and chemical properties of the formation are performed downhole in the coring tool.

As the sample is collected and analyzed at the point of acquisition an archive 38 is created in an electronically accessible database containing a chain-of-custody page, a display of the downhole measurements (summary and graphical displays) with a link to log files, display of the schematic of the petrophysical logs indicating the location of the sample within the reservoir, and a quality assurance page. Wellsite validation and analysis 40 of the sample is performed at the surface, including the condition of the container and container opening pressure. Measurement techniques used at the point of acquisition are repeated at this stage to detect any anomaly in the measurements with reduced uncertainty. Wellsite measurements and analysis are input and documented in the sample database archive 42. If anomalies are noted between the downhole (in-situ) sample measurements and the wellsite sample measurements, the process may be restarted 44. The validated sample is then transported to a laboratory and analyzed 46. Basic analyses are repeated, and specialized studies may be performed. Although different physical techniques may be used to measure sample properties at the point of acquisition, for downhole samples the same procedures as used in the downhole environment are repeated at the wellsite and/or the laboratory to evaluate the quality of the sample, the downhole instruments, and the sampling and handling procedures. All the collected data is input in the sample archive in the database for correlation and validation, step 48. Any discrepancies or anomalies can be noted in the archive for utilization in the flow assurance modeling. At each stage of the process the fingerprint of the sample is checked.

The method of the present invention is described in further detail below. The database facilitates the monitoring of the procedures to ensure the quality of the information obtained. Reservoir property measurements at different stages are displayed in a web-based system for sample quality tracking and analysis. Procedures are also defined for handling conflicting measurements and investigating the causes of the discrepancy. These guidelines are used as the basis for assessments and audits of chain-of-custody procedures to certify samples and measurements, and select with more confidence the reservoir property values to be used for reservoir studies.

Numerous methods may be utilized to obtain the downhole fluid sample(s). The Modular Formation Dynamics Tester (MDT), from Schlumberger, is widely used to acquire downhole fluid samples, and through recent developments performs downhole fluid analysis based on optical spectroscopy methods that enable an early recognition of the fluid characteristics that may affect the acquisition of quality samples. An advantage of downhole fluid analysis is that the fluid is assayed at conditions that are closer to the reservoir conditions, where the fluid has been minimally disturbed from its original conditions. Also, scanning fluid properties at different depths within a geological accumulation prior to the capture of the sample is useful to identify the best sampling depths.

In addition to absorption spectroscopy, other physical techniques may be used to measure fluid properties in the wellbore environment, such as, but not limited to viscosity and optical density with electromechanical systems, dew detection with fluorescence spectroscopy, bubble point pressure with acoustic methods, concentration of hydrogen sulfide with sensors, gas detection with light reflection, pH measurement with chemical reagents and resistivity.

During or immediately after sample acquisition, the wireline sampling tool data channels are processed to extract the recorded and analyzed physical and chemical properties, of the fluid sample at the point of acquisition, such as, but not limited to: "basic information"—date, bottle serial number, sample number, log file name, depth, sampling tool configuration, formation pressure, maximum temperature recorded or formation temperature, mud type, type of sample, type of bottle, bottle opening time, bottle closing time, bottle opening pressure, bottle closing pressure, sample volume, minimum pressure during sample collection, minimum temperature during sample collection; "sample composition"—% by weight of $CO_2$, C1, C2-5, C6+, $H_2S$, gas-oil ratio (GOR), water fraction in the bottle, and apparent hydrocarbon density; "fluid properties"—viscosity, density, bubble point pressure, asphaltene onset pressure, phase transitions, and resistivity; "contamination"—OBM contamination, $CO_2$ decontaminated, C1 decontaminated, C2-5 decontaminated, and C6+ decontaminated; "phase transition indicators"—fluorescence plot, gas detector plot, SDS, SAS, and optical downhole camera; and "quality assurance parameters"—optical absorption spectrum, fluorescence spectrum, viscosity, density, bubble point pressure and gas detector.

Various reservoir formation properties and/or geochemistry properties may be obtained downhole. For example, core mass density data may be obtained by gamma ray attenuation performed in the sidewall coring tool. The photo-electric effect of the core sample may be obtained downhole by measuring the energy dependence of the gamma ray attenuation particularly at low gamma ray energy. Other downhole core measurements may include NMR, acoustics, optical, and electromagnetic. Additionally, fluid flow through the core sample may be measured downhole.

Some of the reservoir formation sample properties may be bulk measurements of the formation sample and some may provide a spatial dependent signal. In particular, as the core is pushed through the core barrel, it may be scanned by a stationary source such as a detector pair. Thus, a core property measurement as a function of linear position along the core may be obtained. NMR measurements conceivably can image part or all of the core sample.

The output of the data processing algorithm is a "Summary Report" that can easily be uploaded into a database.

Since the sample acquisition and downhole analysis information are the first steps in the reservoir characterization process, they initialize a new archive in the database for the particular reservoir being sampled. Successive measurements done either at the wellsite, surface facility, or at the laboratory are input in this archive once they become available. A "Chain-of-Custody" page is also initialized in the sample archive displaying the validating parameters at the different stages (downhole, subsea, wellsite, surface, laboratory) to facilitate sample follow-up and process tracing.

Graphical displays of the downhole data are also loaded into the database since they facilitate the analysis and comparison with laboratory measurements. Useful displays include fluid composition, optical density, mass density, GOR, flowing pressure and temperature versus time, OBM contamination monitoring, fluorescence and gas flag versus time, optical channels, core mass density, and petrophysical logs identifying the sampling locations.

At a given sampling location one or more samples may be obtained. It is very important for chain-of-custody to identify correctly each sample through the serial numbers for traceability at later stages. The database facilitates comparison between samples taken at the same depth, and this may be used as another quality control check.

When the sample reaches the surface, basic Pressure-Volume-Temperature (PVT) laboratory-quality analyses may be performed at the wellsite with PVT Express, from Schlumberger, or other analyses mechanisms, while the downhole fluid analyzer is available to acquire more samples if necessary. The first activity done is the validation of the sample by measuring the sample bottle opening pressure. A value below the indicated sample bottle closing pressure, taking in consideration temperature changes, during the sample acquisition implies that some of the contents of the bottle may have leaked. Similar tests are conducted to validate the core samples obtained.

If bottle opening pressure validation is satisfactory then wellsite fluid analyses will continue, when planned, otherwise the sample will be transferred to the laboratory. The fluid composition, the GOR and the OBM contamination will be measured and compared with downhole measurements. If fluid properties at downhole and at the wellsite or the laboratory disagree, and if no leakage (difference in bottle opening and closing pressures) has been detected, phase transition may be investigated (i.e., sub-sample used for testing may not have been representative). If no phase transition is detected, repeat the downhole measurements in the laboratory to discard problems with tool calibration. All of these validation processes will be stored and commented in the database.

Basically, there are five situations that may render a fluid sample invalid, namely loss of color (loss of components or phase transitions), loss of gas, loss of components, light scattering and disagreement in a channel-by-channel comparison of the optical spectrum. Comparison of optical spectra obtained at downhole condition and in the laboratory gives all the information, and therefore, it is important for chain-of-custody to repeat the same measurements either at the wellsite or at the laboratory using a properly reconditioned sub-sample.

Downhole techniques are reproduced in the laboratory or the wellsite and displayed in the quality assurance section in the database. The laboratory will measure the composition of the fluid with gas and liquid chromatography, or other composition measurement devices. The comparison of the results of different techniques is very instructive. Also the optical absorption spectrum can be measured in the laboratory or at the wellsite with a replica of the downhole spectrometer, or with a different spectrometer.

Replicating downhole measurements in the laboratory or at the wellsite not only validates the samples and certifies compliance with the chain-of-custody, but also helps in the identification and early correction of other problems such as hardware failures, interpretation problems, and inappropriate sampling, sample reconditioning and/or sample transfer techniques.

In order to replicate the downhole optical measurements in the laboratory, samples are reconditioned to reservoir pressure and temperature. For samples that have been in storage, the reconditioning is done for five days prior to the analysis. During this time, the temperature is elevated with a heating jacket. With fluid samples contained in a bottle, the bottle is agitated to homogenize the contents.

Figure 5:
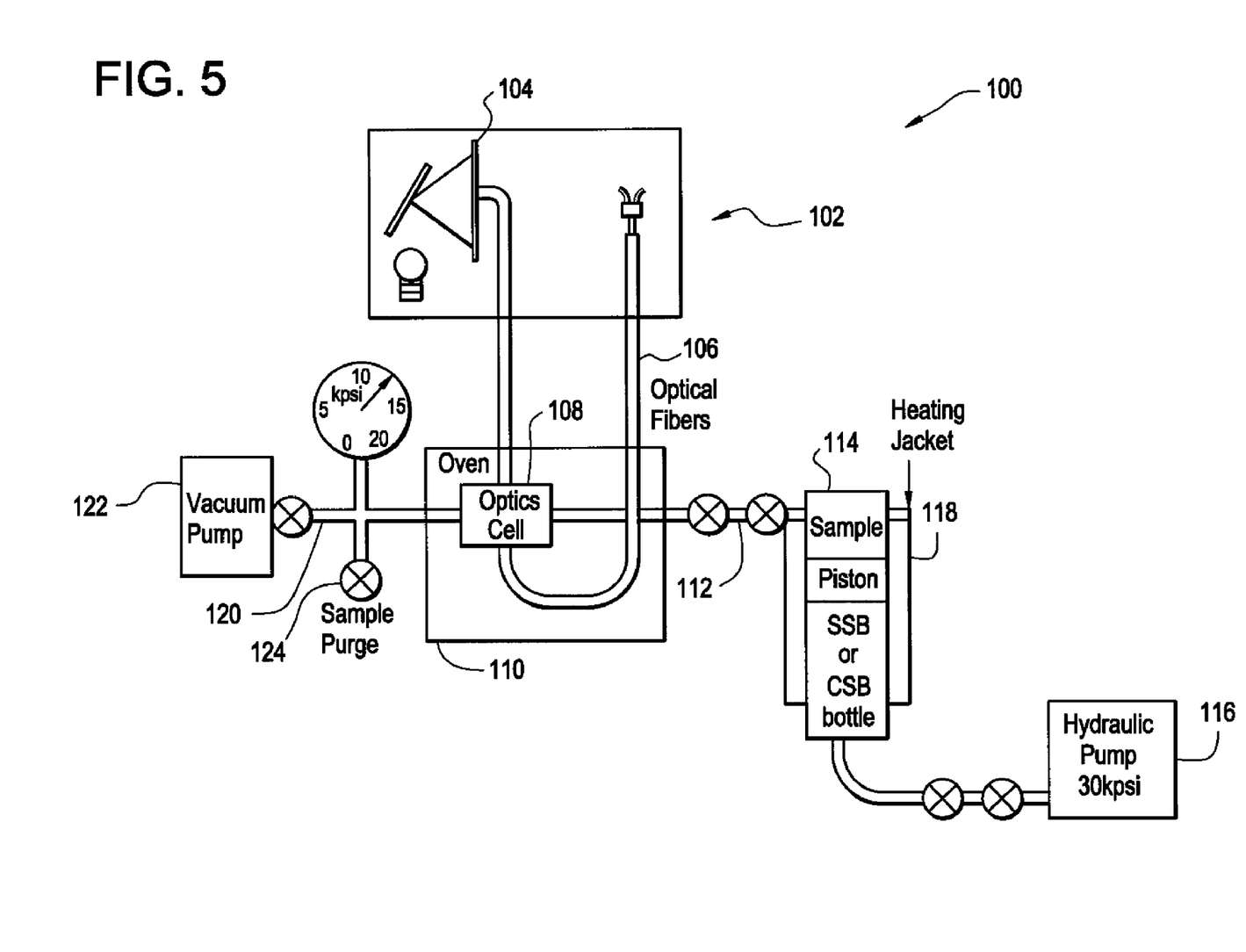
FIG. 5 is a schematic of a laboratory testing system of the present invention.

FIG. 5 is a schematic of a testing system 100 for replicating optical measurements. Optical measurements are conducted with a spectrometer 102, such as a UV-Vis-NIR spectrometer, and a custom made optical board 104 to direct the light beam from spectrometer 102 through 5 mm optical fibers 106 to the high-pressure high-temperature (HPHT) optical cell 108 where the sample is contained and the transmitted light returns to the spectrometer in a similar fashion.

Optical cell 108 has sapphire windows like the downhole tool and a specific pathlength. Optical cell 110 is placed inside an oven 110 where the temperature is adjusted to the temperature of the downhole measurement for that particular sample. A flowline 112 connects optical cell 108 with sample container 114 which is connected to a high-pressure hydraulic pump 116. Sample container 114 is disposed within a heating jacket 118.

A second flowline 102 connects optical cell 108 to a vacuum pump 122 and a purge valve 124. In order to make a measurement, a sample container 114 is attached to the setup with the connecting valves in close position. Hydraulic pump 116 is operated in constant pressure mode and maintained at the pressure of the corresponding downhole measurement for that sample. Once the optical cell 108 and flowlines 112, 114 are evacuated with vacuum pump 122, the valves 126 to container 114 are opened to let the fluid sample into optical cell 108. The dead volumes of the flowlines is about is about 5 cc in the test system. A flash vaporization of the sample in cell 108 and the flowlines occurs during this process, and therefore system 100 must be purged. The contents of optical cell 108 are scanned periodically with spectrometer 102 during this operation and more optical absorption scans are made after the sample has been purged to ensure the stability of the measurement.

Figure 6:
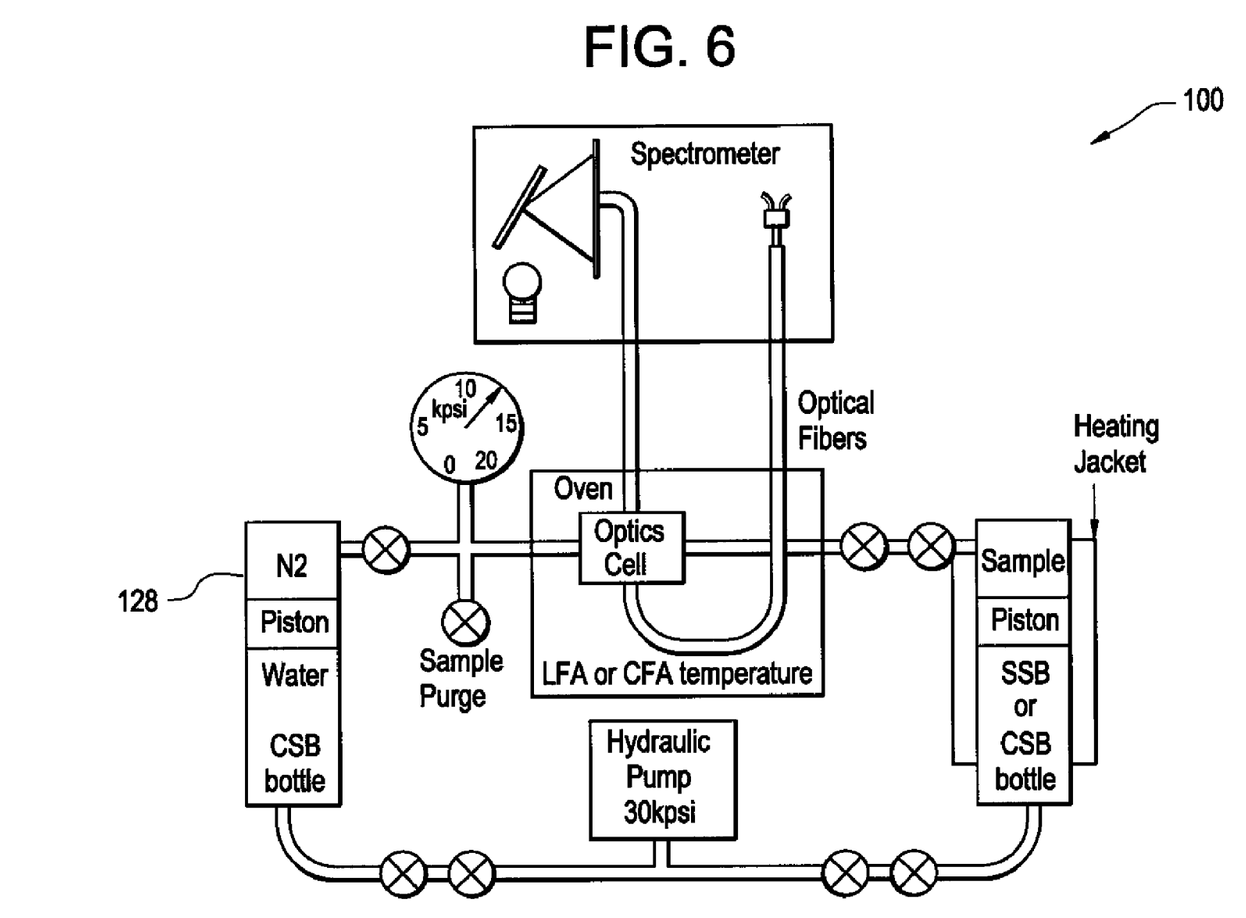
FIG. 6 is a schematic of a modified testing system of the present invention.

Drawbacks of movement of the windows in optical cell 108 and vaporization of the fluid sample when it is transferred to the evacuated system have been recognized in the testing system of FIG. 5. Test system 100 has been modified in the test systems of FIGS. 6 and 7 to address these drawbacks. FIG. 6 is representative of the modifications to address these drawbacks. Vacuum pump 122 has been removed from the system and replaced with pressurized inert gas 128, such as nitrogen. In the modified systems, the flowlines are filled with inert gas, such as nitrogen, at a pressure higher than the saturation pressure of the sample. Inert gasses, such as nitrogen, so not exhibit light absorption characteristics in the wavelength interval of interest.

Figure 7:
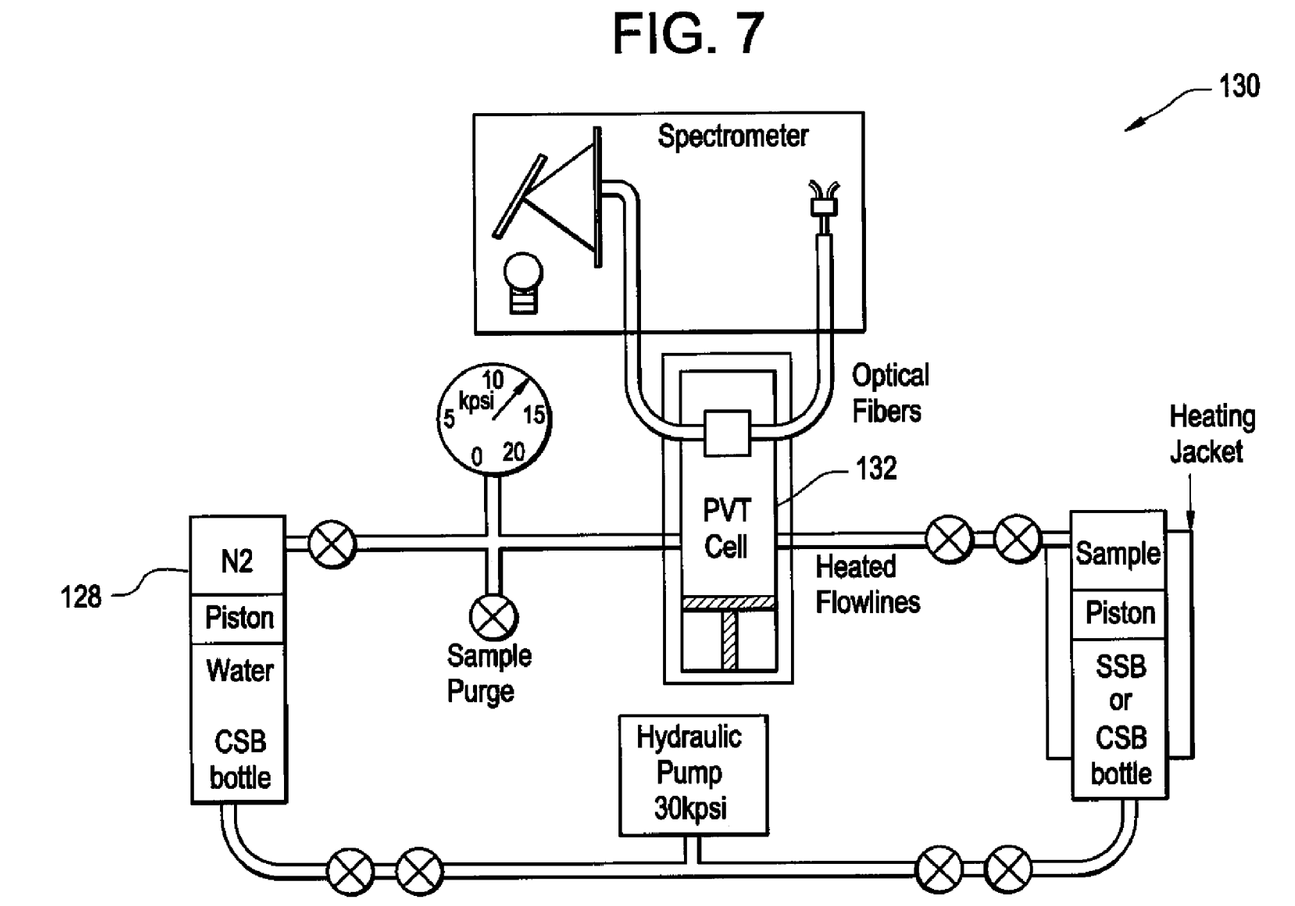
FIG. 7 is a schematic of a comprehensive laboratory testing system of the present invention.

Ideally spectral measurements for chain-of-custody should be integrated with other standard laboratory procedures to streamline laboratory operations. An example of comprehensive testing system is illustrated in FIG. 7. In the comprehensive testing system 130, optical cell 108 of the testing system 100 is replaced with a multiple testing cell 132 such as a PVT/Asphaltene cell with sapphire windows. Cell 132 must be pre-charged with an ultra high purity gas, described as Nitrogen, at reservoir pressure and heated at reservoir temperature before transferring the fluid sample from container 114. Also, the flowlines that connect container 114 and cell 108 must be under temperature control before and during all the time that the measurements are being conducted. This modification reduces the deposition of dropped out asphaltenes on the sapphire cell window of cell 108 by maintaining the bulk fluid above the potential asphaltene envelope. The same optical arrangement described before will direct the incident light from spectrometer 102 to the sample in cell 108 through the cell sapphire windows and channel the transmitted light back to spectrometer 102.

The procedures for measurement are now described generally with reference to FIGS. 5 through 7. The HPHT cell must be cleaned, properly assembled and pressurized to ensure proper seating of the sapphire windows. The optical spectrum [300-2500 nm] of an optical grade reference hydrocarbon (n-heptane) must be measured in a standard glass cuvette and in the HPHT sapphire cell at room pressure and temperature. In both cases the instrument baseline is set to be an empty cell or cuvette. The clean cell is placed in the oven and connected to the flowlines that lead to the sample bottle and the ultra high purity nitrogen. The system is heated to the desired temperature, filled with ultra high purity nitrogen and the pressure is increased above the reservoir pressure of the sample. The valve to the sample container is opened and fluid enters the flowline and the cell. The optical spectrum of the cell contents is measured a couple of times before purging the nitrogen. Two flowline volumes are flushed off the system and the optical spectrum is measured again.

VIS-NIR spectroscopy measurements in a PVT cell 132 as shown in FIG. 7. A lab spectrometer may be linked to a PVT cell to perform spectral measurements during routine PVT analyses. The PVT cell is equipped with an optical window of known pathlength that can be linked to a research grade spectrometer with a custom made optical assembly.

The processing of the spectral data is done in the following order: (1) correction for reflective losses; (2) pathlength correction; (3) elimination of scattering in the downhole signal; (4) GOR calculation; and (5) composition calculation (for GOR>500 sef/stb). The various steps are described below.

Reflective Losses. The baseline for optical measurements is recorded with an empty sample holder (HPHT sapphire cell or glass cuvette). For the case of the HPHT cell, when it is filled with the sample (fluid A), the sapphire-air interface is replaced by sapphire-fluid A. The new fluid has a different refractive index than air, and some light is reflected from each interface. These reflection or Fresnel losses can be calculated to a first-degree approximation using Fresnel formula for normal incidence of non-polarized light.

$$R_F = \left(\frac{n_1 - n_2}{n_1 + n_2}\right)^2 \quad \text{(Eq. 1)}$$

where $n_1$ and $n_2$ are the refractive indexes of the two materials (e.g. sapphire and fluid A). For each sample holder there are two interfaces (eg. Sapphire-fluid-Sapphire), therefore the total reflection loss is $2*R_F$.

For a single n-heptane (n=1.388) and quartz glass (n=1.544) interface, $R_F$=0.0028 or 0.28% of the light reflected on each interface. For the two sample holder interfaces $2*R_F$=0.0057. This translates to an optical density of −0.025. In contrast, with air in the cell, the zeroth order reflective losses in terms of Io are 4.6% at the first interface and 4.4% at the second giving a total loss of ~9.0%, the corresponding OD is 0.041. The difference between an air-filled cell and an n-heptane filled call is ~0.04. Thus, when subtracting the air-filled spectrum, the baseline is negative for the fluid filled cell because of its index matching of the cell.

$$OD = -\log(1 - 2xRF) \quad \text{(Eq. 2)}$$

For n-heptane and sapphire (n=1.74) the OD=−0.11.

The actual reflective losses in the spectra can be determined at wavelengths where no absorption is expected. We use the lowest absorption value of the n-C7 spectrum in the 1000-1300 nm range to define the reflective losses. This measured value correlates well to the calculated value for the glass (quartz) cuvette and is lower for the HPHT cell (sapphire) OD=−0.06. For sapphire-air, the reflective losses are ~7.3% per interface giving an OD of 0.066—again, a yielding a negative baseline for fluid filled cells. The actual reflective losses in the spectra can be measured at wavelengths where no absorption is expected. The smallest negative value of absorption for the n-heptane spectrum in the 1000-1300 nm range is used to define the reflective losses.

Reflective losses do not scale with pathlength, therefore they must be subtracted from the spectral data before doing pathlength correction.

Pathlength Calculation. The downhole spectrometer (live fluid analyzer (LFA) or composition fluid analyzer (CFA)) and the optical cell used in the laboratory have different pathlengths. For comparison, we must convert the lab spectrum to the pathlength of the downhole tool. For the LFA there are variations in the pathlength for each tool, whereas in the case of CFA the OD recorded in the DLIS file is corrected for a pathlength of 2 mm. (U.S. Pat. No. 6,956, 204). The LFA pathlength for each sample analyzed is calculated from the tool calibrations. It is part of the tool calibrations to measure the absorption spectrum of a mineral oil (J26) at room pressure and temperature. One may measure J26 absorption in a standard 2 mm pathlength cuvette in the laboratory. After correcting both spectra for reflective losses once can calculate the pathlength of the LFA as:

$$h_{LFA} = \frac{(OD_{1725} - OD_{1600})_{LFA}}{(OD_{1725} - OD_{1600})_{2\ mm}} * 2.0 \quad \text{(Eq. 3)}$$

In the case of the lab measurements, it is necessary to calculate the pathlength of the HPHT cell every time it is assembled as a quality checkpoint. This is done by measuring the absorption spectrum of spectroscopy grade n-heptane in a 2 mm cuvette and in the HPHT cell at room temperature. Both spectra are corrected for reflective losses and the cell pathlength is calculated as:

$$h_{lab\ cell} = \frac{(OD_{1725} - OD_{1600})_{HPHTcell}}{(OD_{1725} - OD_{1600})_{2\ mm}} * 2.0 \quad \text{(Eq. 4)}$$

Finally the lab spectrum (without Fresnel losses) is multiplied by the ratio $h_{LFA}/_{labcell}$.

Calculation of Simulated Downhole Response from Lab Spectrum. The downhole spectrometers have detectors at specific wavelengths. Each detector has an associated bandwidth to account for spectral shifts. In contrast, the research grade spectrometer in the laboratory is setup to record the optical absorption spectrum of the fluid at 1 nm intervals with a spectral bandwidth of 2 nm.

To convert the lab spectrum to an equivalent downhole spectrum, a filter is applied to the lab data. Gaussian filters have been used with good results:

$$OD_{LFA^*}(k) = \frac{\sum_{i=-n/2}^{n/2} OD_{lab}(k+i)\exp(-i^2/2)}{\sum_{i=-n/2}^{n/2} \exp(-i^2/2)} \quad \text{(Eq. 5)}$$

Where $OD_{LFA}^*$ is the simulated downhole response at wavelength k, with bandwidth n, and $OD_{lab}$ is the lab measurement.

The data could also be filtered in the transmissibility domain:

$$OD_{LFA^*}(k) = \log_{10}\left[\frac{\sum_{i=-n/2}^{n/2} 10^{OD_{lab}(k+i)}\exp(-i^2/2)}{\sum_{i=-n/2}^{n/2} \exp(-i^2/2)}\right] \quad \text{(Eq. 6)}$$

Scattering Calculation. The final step before plotting the downhole and lab spectra is to calculate the scattering in the downhole signal. Usually downhole data present the largest scattering as the fluid being analyzed carries along mud and solid particles that may form a coating on the spectrometer windows. Scattering could be wavelength dependent (more difficult to extract from the signal). Large scattering cross sections are associated with wavelength independence; here we assume it to be wavelength independent.

After accounting for Fresnel losses and correcting for pathlength, the following relation holds for samples that have been preserved properly:

$$OD_{LFA} = OD_{LFA}^* + \text{Scattering} \quad \text{(Eq. 7)}$$

GOR Calculation. The GOR is calculated using the LFA algorithm (See U.S. Pat. Nos. 5,939,717 and 6,956,204):

$$R_{OD} = \frac{OD_{1670} - OD_{1600}}{OD_{1725} - OD_{1600}} \quad \text{(Eq. 8)}$$

$$\frac{m_0}{m_g} = \frac{0.125 - 0.741 * R_{OD}}{0.59 * R_{OD} - 1.177} \quad \text{(Eq. 9)}$$

$$GOR[scf/stb] = 8930 * \frac{\frac{m_o}{m_g}}{1 - 0.193 * \frac{m_o}{m_g}} \quad \text{(Eq. 10)}$$

Crude oils exhibit an exponential decay in their absorption spectrum in the NIR. (See Mullins, O. C., "Optical Interrogation of Aromatic Moieties in Crude Oils and Asphaltenes" in *Structures and Dynamics of Asphaltenes* (O. C. Mullins and E. Y. Sheu, ed) Plenum Press, New York, 1998. In heavy hydrocarbons this behavior impacts considerably the GOR calculation and thus must be accounted for (de-coloration) prior to calculating the GOR. (U.S. Pat. No. 6,274,865). Optical channels with $\lambda < 1600$ nm and OD<3.0 are fit to the following equation to obtain the coefficients C and Eo.

$$OD[\lambda] = C\exp\left(E_o \frac{10^{-7}}{\lambda}\right) \quad \text{(Eq. 11)}$$

where $\lambda$ is the wavelength and $10^{-7}/\lambda$ is the wavenumber

Then the three channels used for the GOR calculation ($\lambda$=1600, 1670, 1725 nm) are corrected as $$OD_{new}[\lambda] = OD[\lambda] - \exp\left[C + E_o \frac{10^{-7}}{\lambda}\right] \quad \text{(Eq. 12)}$$

before applying the LFA algorithm.

CFA algorithm: GOR=5.61*1776*(0.625*C1+0.250*C2+0.227*CO2)/C6; wherein C1, C2-C5, C6+ are the partial densities of methane, ethane-pentane, and hexanes plus.

Composition Calculation. Fluid Composition Y is calculated from the optical spectrum X as Y=b X.

Fluid Composition is at least methane, a group of ethane to pentanes, and a group of heavier components such as C6+. Under some conditions, $CO_2$ concentration could also be determined.

The mathematical procedure for the computation of the fluid composition from optical data is described in U.S. Pat. No. 7,095,012 which is incorporated herein by reference.

Fluid Color. The fluid color can be defined in different ways. It could be the optical absorption value at a given wavelength. It could be the cutoff wavelength for a given optical absorption value, or it could be the fitting parameters of the NIR absorption edge (coefficients C and Eo in equation 11).

Interpretation of Chain-of-Custody Measurements for Sample Validation. The following interpretation criteria is based on the use of five measurements: Downhole GOR, Lab Spectrum GOR, Lab GOR, Lab Color, Downhole Color.

TABLE 1

| Case | Situation | Diagnosis | Actions |
|---|---|---|---|
| 1 | Lab spectrum GOR = | Sample has been well | None |

TABLE 1-continued

| Case | Situation | Diagnosis | Actions |
|------|-----------|-----------|---------|
|  | Dowhole GOR = Lab GOR | preserved |  |
| 2 | Lab spectrum GOR = Lab GOR > Downhole GOR | Possible Calibration issues with DFA | Review lab and DFA GOR on other samples analyzed with the same tool to identify trends |
| 3 | Lab Spectrum GOR = Downhole GOR ≠ Lab GOR | Sample has been well preserved | Review measurement conditions of lab GOR. Account for the influence of intermediate gases (C2-C5) in the GOR calculation. Could use lab GC fluid composition to calculate GOR using DFA algorithms. Review lab and DFA GOR on other samples analyzed with the same tool to identify trends |
| 4 | Lab spectrum GOR = Lab GOR < Downhole GOR | Possible sample leak Possible calibration issues | Review lab and DFA GOR on other samples analyzed with the same tool to identify trends. If tool calibration problems are discarded, then sample may have leaked. |
| 5 | Lab Color = Downhole Color | Sample has been well preserved | None |
| 6 | Lab Color ≠ Downhole Color | Possible loss of heavy components Possible calibration issues | Review lab and downhole color on other samples analyzed with the same DFA to identify trends. If tool calibration problems are discarded, then heavy components might have been lost. |

Even though the equality sign is used in the above algorithm, it must be kept in mind that the values used for this analysis proceed from different tools and techniques and the intrinsic measurement errors should be taken into account for the comparison.

From the foregoing detailed description of specific embodiments of the invention, it should be apparent that a chain-of-custody process that is novel has been disclosed. Although specific embodiments of the invention have been disclosed herein in some detail, this has been done solely for the purposes of describing various features and aspects of the invention, and is not intended to be limiting with respect to the scope of the invention. It is contemplated that various substitutions, alterations, and/or modifications, including but not limited to those implementation variations which may have been suggested herein, may be made to the disclosed embodiments without departing from the spirit and scope of the invention as defined by the appended claims which follow.

What is claimed is:

1. A method of assuring acquisition of a representative sample of a reservoir formation from a wellbore, the method comprising the steps of:
   acquiring a reservoir formation sample having a formation sample property;
   measuring the formation sample property at a point of acquisition in the wellbore with a technique to obtain a measured point of acquisition property;
   measuring the formation sample property at a remote location from the point of acquisition with a technique to obtain a measured remote location property; and
   validating the formation sample by comparing the measured point of acquisition property to the measured remote location property.

2. The method of claim 1, wherein the reservoir formation sample is a sidewall core.

3. The method of claim 1, the formation sample property is mass density.

4. The method of claim 3, wherein the reservoir formation sample is a sidewall core.

5. The method of claim 1, wherein the measured remote location property is obtained by replicating the measuring technique utilized to obtain the measure point of acquisition property.

6. The method of claim 1, wherein the measuring technique includes at least one of gamma ray attenuation, nuclear magnetic resonance, acoustics, optical or electromagnetic.

7. The method of claim 1, wherein the step of validating includes at least one of confirming the provenance of the formation sample, confirming correspondence of the measured remote location property with the measured point of acquisition property, or transformation of the formation sample since acquisition of the formation sample.

8. The method of claim 7, wherein the reservoir formation sample is a sidewall core.

9. The method of claim 1, further including the steps of:
   recording the measured point of acquisition property in an electronic database archive;
   recording the measured remote location property in the archive; and
   providing a chain-of-custody page by the archive displaying validating parameters for the formation sample.

10. The method of claim 9, wherein the reservoir formation sample is a sidewall core.

11. The method of claim 1, wherein:
   the reservoir formation sample is a sidewall core;
   the formation sample property is mass density; and
   the measured remote location property is obtained by replicating the measuring technique utilized to obtain the measure point of acquisition property.

12. The method of claim 11, further including the steps of:
   recording the measured point of acquisition property in an electronic database archive;
   recording the measured remote location property in the archive; and
   providing a chain-of-custody page by the archive displaying validating parameters for the formation sample.

13. A method of assuring acquisition of a representative sample of a subsurface reservoir from a wellbore, the method comprising the steps of:
   acquiring a reservoir formation sample having a formation sample property;
   measuring the formation sample property at a point of acquisition in the wellbore with a technique to obtain a measured point of acquisition formation property;
   measuring the formation sample property at a remote location from the point of acquisition with a technique to obtain a measured remote location formation property;
   validating the formation sample by comparing the measured point of acquisition property to the measured remote location property;
   recording formation sample validating parameter in a database archive;
   acquiring a reservoir fluid sample in the wellbore;
   measuring a property of the fluid sample downhole with a technique to obtain a measured downhole fluid property;

measuring the property of the fluid sample at a remote location from the wellbore with a technique to obtain a measured remote location fluid property;

validating the fluid sample through comparison of the measured downhole fluid property and the measured remote location fluid property; and recording fluid sample validating parameter in the archive.

14. The method of claim 13, further including the steps of:

recording the measured point of acquisition formation property in the archive;

recording the measured remote location formation property in the archive;

recording the measured downhole fluid property in the archive; and recording the measured remote location fluid property in the archive.

15. The method of claim 13, further including the step of providing a chain-of-custody page by the archive displaying the formation sample validating parameter and the fluid sample validating parameter.

16. The method of claim 15, wherein the database archive is web-based.

17. The method of claim 13, wherein the database archive is web-based.

18. The method of claim 13, wherein:

the measured downhole fluid property includes downhole gas-oil ratio; and the measured remote location fluid property includes lab spectrum gas-oil ratio and lab gas-oil ratio.

19. The method of claim 18, wherein the step of validating the fluid sample includes the step of identifying measuring technique trends if the lab gas-oil ratio does not substantially equal the measured downhole gas-oil ratio.

20. The method of claim 13, wherein the fluid sample validating parameter includes one of substantial correspondence between the measured downhole fluid property and the measured remote location fluid property or an identified supporting measuring technique trend.

21. A method of validating a reservoir fluid sample obtained from a wellbore, the method comprising the steps of:

acquiring a reservoir fluid sample in the wellbore;

measuring a property of the fluid sample downhole with a technique to obtain a measured downhole fluid property;

replicating the measuring technique used to obtain the measured downhole fluid property to obtain at a remote location from the wellbore with a technique to obtain at least one measured remote location fluid property; and validating the fluid sample through comparison of the measured downhole fluid property and the at least one measured remote location fluid property.

22. The method of claim 21, further including the steps of:

recording the validated fluid sample property in a web-based archive; and providing a chain-of-custody page by the archive displaying the validated fluid sample property.

23. The method of claim 21, wherein the step of validating includes the step of identifying measuring technique trends if the measured downhole fluid property and at least one of the at least one measured remote location fluid sample properties do not substantially correspond.

24. The method of claim 21, wherein the measured downhole fluid property is gas-oil ratio and the at least one measured remote location fluid property includes lab gas-oil ratio and lab spectrum gas-oil ratio.

25. The method of claim 24, wherein the step of validating the fluid sample includes the step of identifying measuring technique trends if the lab gas-oil ratio does not substantially equal the measured downhole gas-oil ratio.

26. The method of claim 21, wherein the replicating step includes the step of converting a pathlength of the remote location measuring technique to substantially match a pathlength the downhole measuring technique.

27. The method of claim 21, wherein the replicating step includes the steps of correcting spectral data of the remote location measuring technique to correspond with the downhole measuring technique.

28. The method of claim 21, wherein the step of correcting the spectral data includes the steps of:

correcting for reflective losses;

correcting pathlength; and eliminating scattering in the downhole measuring technique.

29. The method of claim 21, wherein the replicating step includes:

providing a remote location testing system having a spectrometer functionally connected to a multiple testing cell having sapphire windows;

connecting the fluid sample in the testing system;

reconditioning the fluid sample to reservoir pressure and temperature;

charging the testing system with a pressurized inert gas at the reservoir pressure and temperature;

purging the inert gas from the system;

introducing the fluid sample into the cell; and obtaining the at least one measured remote location fluid property with the spectrometer.

* * * * *